United States Patent
Teshigawara

(10) Patent No.: US 11,796,694 B2
(45) Date of Patent: Oct. 24, 2023

(54) PET APPARATUS, METHOD, AND RECORDING MEDIUM

(71) Applicant: CANON MEDICAL SYSTEMS CORPORATION, Tochigi (JP)

(72) Inventor: Manabu Teshigawara, Otawara (JP)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 0 days.

(21) Appl. No.: 17/653,533

(22) Filed: Mar. 4, 2022

(65) Prior Publication Data

US 2022/0283326 A1   Sep. 8, 2022

(30) Foreign Application Priority Data

Mar. 4, 2021 (JP) ................. 2021-034629

(51) Int. Cl.
*G01T 7/00* (2006.01)
*G01T 1/29* (2006.01)
*A61B 6/03* (2006.01)
*A61B 6/00* (2006.01)

(52) U.S. Cl.
CPC .............. *G01T 7/00* (2013.01); *A61B 6/037* (2013.01); *A61B 6/586* (2013.01); *G01T 1/2985* (2013.01)

(58) Field of Classification Search
CPC ......... G01T 7/00; G01T 1/2985; A61B 6/037; A61B 6/586; G06T 11/005
See application file for complete search history.

(56) References Cited

U.S. PATENT DOCUMENTS

| | | | |
|---|---|---|---|
| 5,703,369 A * | 12/1997 | Mori ............. | A61B 6/037 250/363.09 |
| 9,606,245 B1 | 3/2017 | Czarnecki et al. | |
| 9,835,737 B1 | 12/2017 | Czarnecki et al. | |
| 2009/0224164 A1 | 9/2009 | Lewellen et al. | |
| 2018/0059267 A1 | 3/2018 | Ng et al. | |
| 2020/0352537 A1* | 11/2020 | Bai ............. | A61B 6/5235 |

FOREIGN PATENT DOCUMENTS

JP        2001208849 A  *  8/2001

* cited by examiner

*Primary Examiner* — David P Porta
*Assistant Examiner* — Casey Bryant
(74) *Attorney, Agent, or Firm* — Oblon, McClelland, Maier & Neustadt, L.L.P.

(57) ABSTRACT

A Positron Emission Tomography (PET) apparatus according to an embodiment includes processing circuitry. The processing circuitry is configured to obtain information about a defective channel of a PET detector at a second point in time later than a first point in time corresponding to a first sensitivity map that is a sensitivity map of the PET detector corresponding to the first point in time and being stored in a storage unit. The processing circuitry is configured to generate a second sensitivity map that is a sensitivity map of the PET detector corresponding to the second point in time, on the basis of the information about the defective channel.

12 Claims, 8 Drawing Sheets

PET APPARATUS, METHOD, AND RECORDING MEDIUM

CROSS-REFERENCE TO RELATED APPLICATIONS

This application is based upon and claims the benefit of priority from Japanese Patent Application No. 2021-034629, filed on Mar. 4, 2021; the entire contents of which are incorporated herein by reference.

FIELD

Embodiments described herein relate generally to a Positron Emission Tomography (PET) apparatus, a method, and a recording medium.

BACKGROUND

A Positron Emission Tomography (PET) detector employed in a PET apparatus includes a scintillator array and an optical detector array. The scintillator array is structured with a plurality of scintillators. The optical detector array is structured with a plurality of optical detectors (optical detecting elements). In this regard, for example, the optical detector array may be structured, in some situations, with a plurality of Photomultiplier Tubes (PMTs) serving as the plurality of optical detectors. A PET apparatus including such an optical detector array may adopt a multiplex method, for example. In this situation, in the entire PET detector, the number of channels (a total number of signal output channels) is approximately hundreds, because the quantity of the PMTs is smaller than the quantity of a large number of scintillators structuring the scintillator array.

Because fluorescent light from the large number of scintillators becomes incident to the smaller number of PMTs and is converted into signals, if a signal output from one of the PMTs has a loss, a non-negligible impact is made on a large part of an image. Accordingly, during a health check to diagnose (to inspect) a failure of PET detectors, taking an actual image of a phantom makes it qualitatively clearer whether a failure is present or absent than when a user visually inspects images. For this reason, when a PET detector fails, there is no other option besides repairing or replacing the PET detector. In this sense, there is no need to make special judgment.

In another example, the optical detector array may be structured, in some situations, with a plurality of Silicon Photomultipliers (SiPMs) serving as the plurality of optical detectors. In this example, each of the scintillators may be optically coupled with a different one of the SiPMs (i.e., the scintillators and the SiPMs are in one-to-one optical coupling) or each group of a small number of scintillators may be optically coupled with a different one of the SiPMs. Accordingly, the number of independent channels (the number of signal output channels) in the entire PET detector is as many as tens of thousands to hundreds of thousands. If the channels include one or more defective channels, changes in or impacts on image quality of images are not so significant as to be immediately noticed in visual inspection of users unlike in the example of the PET detector in which the plurality of PMTs are used in the optical detector array and may vary depending on the quantity of the defective channels and the relative positions of the defective channels within the PET detector. In this situation, the term "defective channels" denotes channels corresponding to failed optical detectors, for example. Changes in uniformity of an image do not necessarily occur evenly in a large area and may occur in units of pixels or in a component. For this reason, the visual inspection method to inspect an image that is obtained by imaging a phantom and contains statistical noise lacks in quantitativeness and objectiveness. In other words, when each of the scintillators is optically coupled with a different one of the SiPMs or when each group of a small number of scintillator is optically coupled with a different one of the SiPMs, because the impact on the image quality (or the image) imposed by individual channel defects is relatively minor, criteria used for determining countermeasures are not definitive.

Accordingly, with regard to PET detectors having a large number of independent channels, there is a demand for quantitatively and objectively evaluating impacts on image quality imposed by defective channels. It is important that users correctly determine countermeasures on the basis of such an evaluation, from the viewpoint of guaranteeing safety and capabilities in the clinical field and from the viewpoint of properly allocating costs in the fields of manufacturing and services.

DETAILED DESCRIPTION

One of the problems to be solved by the embodiments disclosed in the present specification and drawings is to quantitatively and objectively evaluate impacts on image quality imposed by defective channels. However, possible problems to be solved by the embodiments disclosed in the present specification and drawings are not limited to the problem stated above. It is also possible to consider any of the problems corresponding to advantageous effects achieved by the configurations described in the embodiments presented below, as other problems.

A PET apparatus according to an embodiment includes processing circuitry. The processing circuitry is configured to obtain information about a defective channel of a PET detector at a second point in time later than a first point in time corresponding to a first sensitivity map that is a sensitivity map of the PET detector corresponding to the first point in time and being stored in a storage unit. The processing circuitry is configured to generate a second sensitivity map that is a sensitivity map of the PET detector corresponding to the second point in time, on the basis of the information about the defective channel.

Exemplary embodiments of a PET apparatus, a method, and a computer program (hereinafter, "program") will be explained in detail below, with reference to the accompanying drawings. The PET apparatus, the method, and the program of the present disclosure are not limited to the embodiments described below. Further, the description of each of the embodiments is, in principle, similarly applicable to any other embodiment or modification example. Also, the description of each of the modification examples is, in principle, similarly applicable to any of the embodiments and the other modification examples.

First Embodiment

Figure 1:
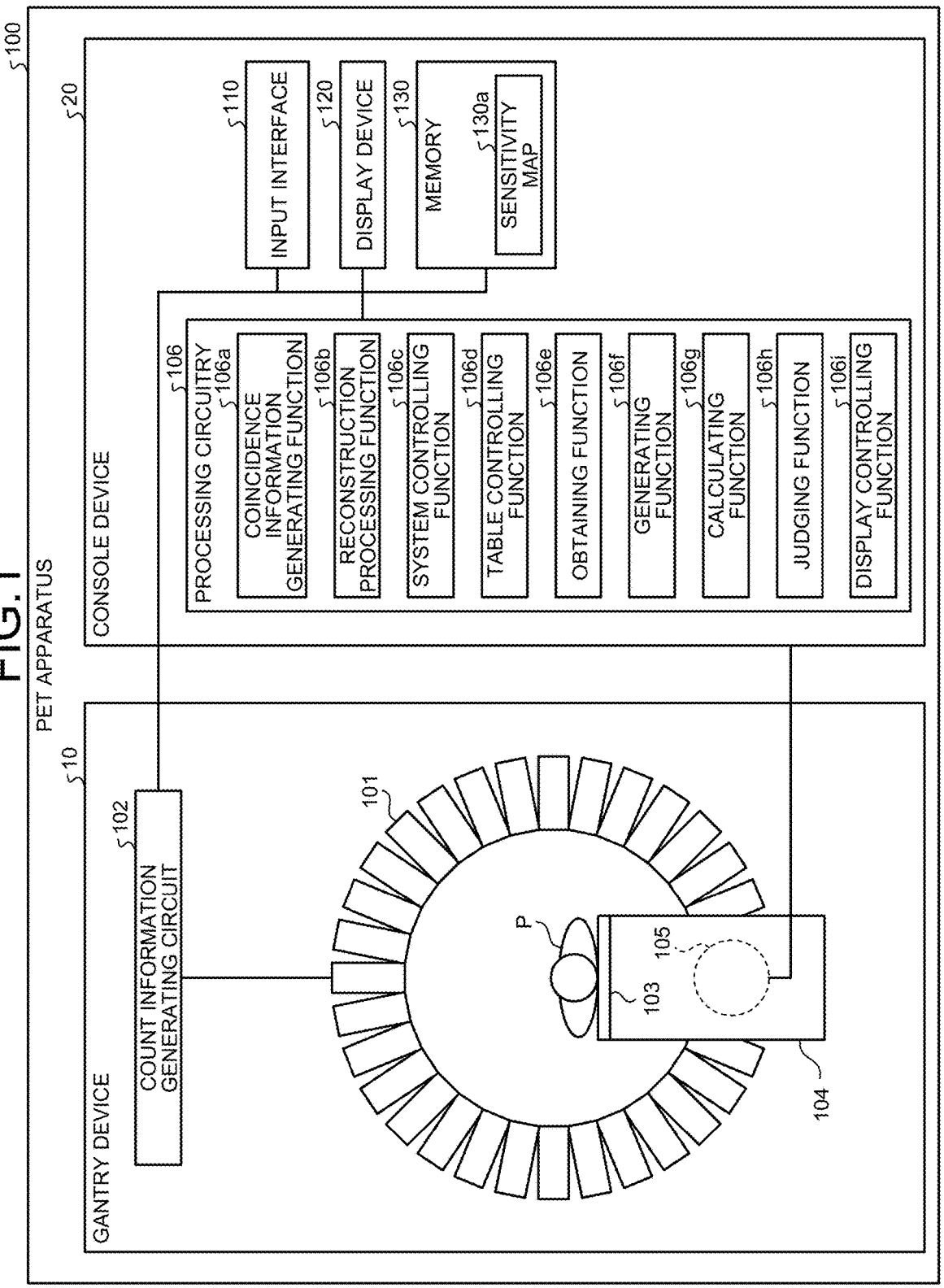
FIG. 1 is a diagram illustrating an exemplary configuration of a PET apparatus according to a first embodiment.

FIG. 1 is a diagram illustrating an exemplary configuration of a PET apparatus 100 according to a first embodiment. As illustrated in FIG. 1, the PET apparatus 100 according to the first embodiment includes a gantry device 10 and a console device 20. For instance, the PET apparatus 100 is an example of a nuclear medicine diagnosis apparatus.

The gantry device 10 includes a PET detector 101, a count information generating circuit 102, a tabletop 103, a table 104, and a table driving unit 105.

The PET detector 101 includes a plurality of detector modules. The plurality of detector modules are configured to detect radiation by detecting scintillation photons (fluorescent light) that are re-released when a substance in an excited state transitions back into a ground state as a result of an interaction between annihilation gamma rays released from positrons inside an examined subject (hereinafter, "patient") P and a light emitting bodies (the scintillators). The plurality of detector modules are configured to detect radiation energy information of the annihilation gamma rays released from the positrons inside the patient P. The plurality of detector modules are arranged so as to surround the patient P in a ring formation.

Each of the detector modules includes, for example, a scintillator array, an optical detector array, and a light guide.

The scintillator array includes a plurality of scintillators arranged two-dimensionally. The scintillators are configured to convert annihilation gamma rays that have become incident thereto after being released from the positrons inside the patient P, into scintillation photons (or optical photons) and to output the scintillation photons. The scintillators are formed with scintillator crystals that are suitable for a Time Of Flight (TOF) measuring process or an energy measuring process, such as those of Lanthanum Bromide (LaBr3), Lutetium Yttrium Oxyorthosilicate (LYSO), Lutetium Oxyorthosilicate (LSO), or Lutetium Gadolinium Oxyorthosilicate (LGSO), for example.

The light guide is formed by using a plastic material or the like having excellent light transmittance and is configured to transfer the scintillation photons output from the scintillators to the optical detectors. More specifically, the light guide is configured to transfer the scintillation photons to Silicon Photomultipliers (SiPMs) explained later.

The optical detector array includes a plurality of optical detectors (optical detecting elements) arranged two-dimensionally. For example, the SiPMs may be used as the optical detectors. In the present embodiment, each of the scintillators is optically coupled with a different one of the SiPM. In other words, the scintillators and the SiPMs are in one-to-one optical coupling. In this situation, a set made up of one scintillator and one SiPM optically coupled with the one scintillator corresponds to one channel. Alternatively, a small number of scintillators may be optically coupled with a SiPM. In that situation, a set made up of the small number of scintillators and one SiPM optically coupled with the small number of scintillators corresponds to one channel. In either situation, the number of channels (the number of signal output channels) in the entirety of the PET detector 101 is as many as tens of thousands to hundreds of thousands. The SiPMs are configured to detect the scintillation photons emitted by the scintillators, to generate an electrical signal corresponding to the scintillation photons, and to output the generated electrical signal as an output signal.

The PET detector 101 is provided with the count information generating circuit 102 for each of the detector modules.

The count information generating circuit 102 is configured to generate digital data as count information, by converting the output signal from the PET detector 101 into the digital data. The count information includes detection positions of the annihilation gamma rays, energy values, and detection times. For example, the count information generating circuit 102 identifies a plurality of optical detectors that converted scintillation photons into electrical signals at mutually the same time. Further, the count information generating circuit 102 identifies scintillator numbers (P) indicating the positions of the scintillators (scintillator positions) to which the annihilation gamma rays became incident. The count information generating circuit 102 may use any of various methods, as the method for identifying the scintillator positions in which the annihilation gamma rays became incident. For example, because each one of the scintillators corresponds to a different one of the SiPMs, the count information generating circuit 102 may identify the position of a scintillator corresponding to a SiPM from which an output was obtained, as the scintillator position in which the annihilation gamma rays became incident.

Further, the count information generating circuit 102 is configured to identify energy values (E) of the annihilation gamma rays that became incident to the PET detector 101, through an integral calculation on intensities of the electrical signals output from the optical detectors. Further, the count information generating circuit 102 is configured to identify detection times (T) at which the scintillation photons from the annihilation gamma rays were detected by the PET detector 101. The detection times (T) may be absolute times or elapsed time periods since the start of the imaging process. As explained herein, the count information generating circuit 102 is configured to generate the count information including the scintillator numbers (P), the energy values (E), and the detection times (T). Further, the count information generating circuit 102 is configured to store the generated count information into a memory 130 of the console device 20.

For example, the count information generating circuit 102 is realized by using a processor.

The tabletop 103 is a bed on which the patient P is placed and is arranged over the table 104. The table driving unit 105 is configured to move the tabletop 103 under control of a table controlling function 106d of processing circuitry 106.

For example, the table driving unit 105 is configured to move the patient P to the inside of an imaging opening of the gantry device 10, by moving the tabletop 103.

Upon receipt of an operation performed by a user on the PET apparatus 100, the console device 20 is configured to control imaging of PET image data and to reconstruct (generate) the PET image data by using the count information acquired by the gantry device 10. As illustrated in FIG. 1, the console device 20 includes the processing circuitry 106, an input interface 110, a display device 120, and the memory 130. In this situation, the processing circuitry 106, the input interface 110, the display device 120, and the memory 130 are connected together via a bus.

The processing circuitry 106 includes a coincidence information generating function 106a, a reconstruction processing function 106b, a system controlling function 106c, the table controlling function 106d, an obtaining function 106e, a generating function 106f, a calculating function 106g, a judging function 106h, and a display controlling function 106i. The functions such as the coincidence information generating function 106a, the reconstruction processing function 106b, the system controlling function 106c, the table controlling function 106d, the obtaining function 106e, the generating function 106f, the calculating function 106g, the judging function 106h, and the display controlling function 106i are stored in the memory 130 in the form of computer-executable programs. The processing circuitry 106 is a processor configured to realize the functions corresponding to the programs, by reading the programs from the memory 130 and executing the read programs. In other words, the processing circuitry 106 that has read the programs has the functions illustrated within the processing circuitry 106 in FIG. 1. With reference to FIG. 1, the example was explained in which the single piece of processing circuitry (i.e., the processing circuitry 106) realizes the coincidence information generating function 106a, the reconstruction processing function 106b, the system controlling function 106c, the table controlling function 106d, the obtaining function 106e, the generating function 106f, the calculating function 106g, the judging function 106h, and the display controlling function 106i. However, another arrangement is also acceptable in which the processing circuitry 106 is structured with a plurality of independent processors, so that the functions are realized as a result of the processors executing the programs.

In this situation, for instance, the reconstruction processing function 106b is an example of a reconstruction processing unit. For instance, the obtaining function 106e is an example of an obtaining unit. For instance, the generating function 106f is an example of a generating unit. For instance, the calculating function 106g is an example of a calculating unit. For instance, the judging function 106h is an example of a judging unit. For instance, the display controlling function 106i is an example of a display controlling unit.

The term "processor" used in the above explanation denotes, for example, a Central Processing Unit (CPU), a Graphical Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors are configured to realize the functions by reading the programs saved in the memory 130 and executing the read programs.

The coincidence information generating function 106a is configured to obtain the count information stored in the memory 130 and to generate pieces of coincidence information on the basis of the obtained count information. Further, the coincidence information generating function 106a is configured to arrange the generated pieces of coincidence information in a substantially chronological order on the basis of the detection times (T) and to store the arranged information into the memory 130. As a result, the memory 130 has stored therein a time-series list of the coincidence information.

The reconstruction processing function 106b is configured to reconstruct the PET image data. For example, the reconstruction processing function 106b is configured to obtain the time-series list of the coincidence information stored in the memory 130 and to reconstruct the PET image data by using the obtained time-series list of the coincidence information. Further, the reconstruction processing function 106b is configured to store the reconstructed PET image data into the memory 130.

The system controlling function 106c is configured to control the entirety of the PET apparatus 100, by controlling the gantry device 10 and the console device 20. For example, the system controlling function 106c is configured to control imaging processes performed by the PET apparatus 100.

The table controlling function 106d is configured to control the moving of the tabletop 103, by controlling the table driving unit 105. The obtaining function 106e, the generating function 106f, the calculating function 106g, and the judging function 106h will be explained later.

The display controlling function 106i is configured to cause the display device 120 to display various types of images and various types of information. For example, the display controlling function 106i is configured to cause the display device 120 to display a PET image based on the PET image data. Also, the display controlling function 106i is configured to cause the display device 120 to display a Graphical User interface (GUI) used for receiving various types of instructions and various types of settings from the user (an operator) of the PET apparatus 100.

The input interface 110 is configured to receive the inputs of the various types of instructions and the various types of settings from the user and to output the received various types of instructions and various types of settings to the processing circuitry 106. For example, the input interface 110 is configured to convert the input operations received from the user into electrical signals and to transmit the electrical signals to the processing circuitry 106. For example, the input interface 110 is realized by using a trackball, a switch button, a mouse, a keyboard, a touchpad on which input operations can be performed by touching an operation surface thereof, a touch screen in which a display screen and a touchpad are integrally formed, a contactless input circuit using an optical sensor, an audio input circuit, and/or the like. In the present disclosure, the input interface 110 does not necessarily have to include physical operation component parts such as a mouse, a keyboard, and/or the like. For instance, possible examples of the input interface 110 include electrical signal processing circuitry configured to receive an electrical signal corresponding to an input operation from an external input device provided separately from the PET apparatus 100 and to transmit the electrical signal to the processing circuitry 106. For instance, the input interface 110 is an example of a receiving unit.

The display device 120 is connected to the processing circuitry 106 and is configured to display the various types of information and the various types of information. For example, the display device 120 is configured to convert information and data transmitted thereto from the processing circuitry 106 into display-purpose electrical signals and to output the electrical signals. In a specific example, under the control of the display controlling function 106i, the display device 120 is configured to display the PET image based on the PET image data and to display the GUT used for receiving the various types of instructions and the various types of settings from the user. For example, the display device 120 is realized by using a liquid crystal monitor, a Cathode Ray Tube (CRT) monitor, a touch panel, or the like. The display device 120 is an example of a display unit.

The memory 130 is configured to store therein various types of data used in the PET apparatus 100. The memory 130 is an example of the storage unit. For example, the memory 130 is realized by using a semiconductor memory element such as a Random Access Memory (RAM) or a flash memory, or a hard disk, an optical disk, or the like. The memory 130 is configured to store therein the count information which is the information in which the scintillator numbers (P), the energy values (E), and the detection times (T) are kept in correspondence with one another, the time-series list of the coincidence information in which coincidence numbers serving as serial numbers of the pieces of coincidence information are kept in correspondence with sets of count information, the reconstructed PET image data, and the like.

Figure 2:
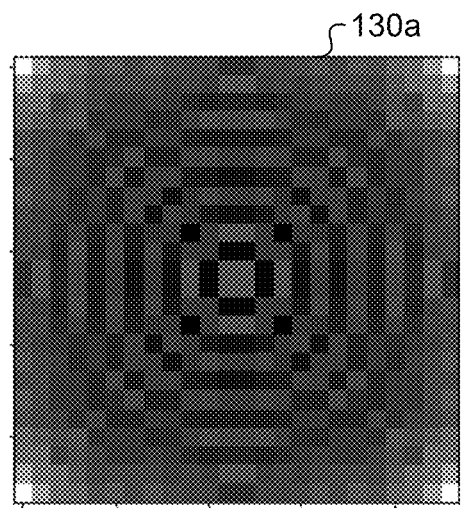
FIG. 2 is a drawing illustrating an example of a sensitivity map according to the first embodiment.

Further, the memory 130 is configured to store therein a sensitivity map 130a. FIG. 2 is a drawing illustrating an example of the sensitivity map 130a according to the first embodiment. The sensitivity map 130a indicates sensitivity of the PET detector 101 with respect to each of the pixels in a region (a reconstruction region) subject to a reconstructing process. The pixel size may be 4 mm×4 mm, for example, but the pixel size is not limited to this example. The sensitivity map 130a is obtained when the PET detector 101 has no failure, so that all the channels of the PET detector 101 are normal channels without being defective channels. In other words, the sensitivity map 130a is a sensitivity map of the PET detector 101 corresponding to a point in time when all the channels of the PET detector 101 are normal channels. For example, the sensitivity map 130a is an example of the first sensitivity map. Further, the point in time when all the channels of the PET detector 101 are normal channels is an example of the first point in time.

Next, an example of a method for generating the sensitivity map 130a will be explained. The sensitivity map 130a may be generated by the PET apparatus 100 or may be generated by an apparatus other than PET apparatus 100. In the following explanations, an example will be explained in which the generating function 106f of the PET apparatus 100 is configured to generate the sensitivity map 130a.

Figure 3:
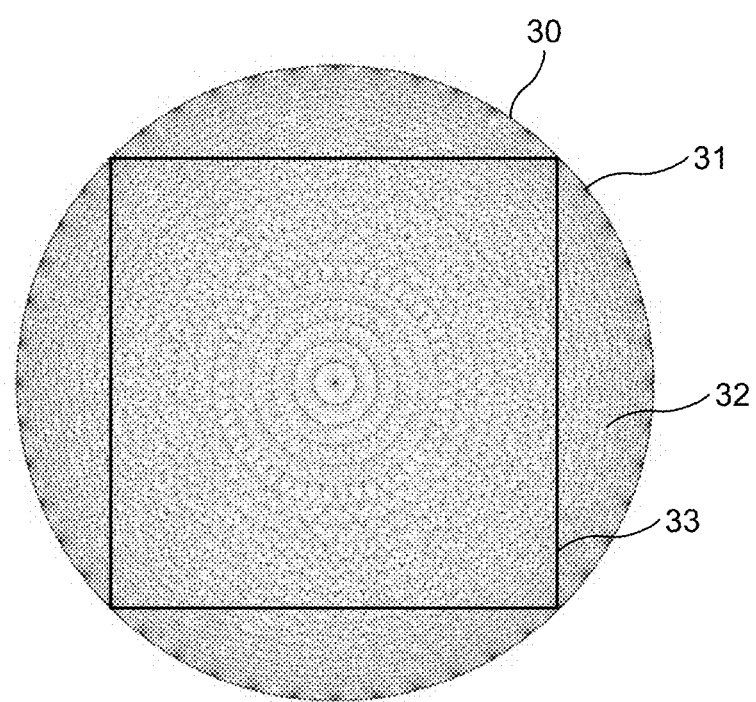
FIG. 3 is a drawing for explaining an example of a method for generating the sensitivity map according to the first embodiment.

FIG. 3 is a drawing for explaining an example of the method for generating the sensitivity map 130a according to the first embodiment. As illustrated in FIG. 3, the generating function 106f is configured to generate a model 30 of the PET detector 101 in which models of the plurality of detector modules are arranged in a ring formation.

In the example in FIG. 3, the generating function 106f is configured to generate the model 30 of the PET detector 101 in which the models of 48 detector modules are arranged in the ring formation. The model of each of the detector modules includes at least one set 31 made up of a model of one scintillator and a model of one SiPM. For example, it is preferable when the quantity and the positional arrangements of the sets 31 included in the model 30 are the same as the quantity and the positional arrangements of sets that are each made up of one scintillator and one SiPM and are included in the PET detector 101. For example, it is preferable when the quantity of the sets 31 included in the model 30 is a number between tens of thousands and hundreds of thousands that is equal to the quantity of the sets that are each made of one scintillator and one SiPM and are included in the PET detector 101.

However, for the sake of convenience in the explanation, the following will explain an example in which the model of each of the detector modules includes only one set 31. In other words, in the model 30 of the PET detector 101 illustrated in FIG. 3, 48 sets 31 are arranged in the ring formation. In this situation, the number of channels in the model 30 of the PET detector 101 is "48". In the present example, all the channels are normal channels. Further, the 48 channels are identified with identifiers "1" to "48", respectively.

Further, the generating function 106f is configured to draw a Line Of Response (LOR) 32 connecting two channels among the 48 channels, with respect to every combination each made up of two channels. In the example in FIG. 3, the generating function 106f is configured to draw 1,128 (=48×47/2) LORs 32. A pattern of the LORs 32 drawn in this manner may be referred to as an LOR pattern.

As illustrated in FIG. 3, the density of the LORs 32 is not uniform. There are regions where the density of the LORs 32 is relatively low and where the density is relatively high. Annihilation gamma rays emitted from a high-density region are detected more than annihilation gamma rays emitted from a low-density region. In other words, a high-density region has a higher possibility of the occurrence of annihilation than a low-density region.

Further, the generating function 106f is configured to generate the sensitivity map 130a, by converting the LOR pattern in a reconstruction region 33 of the model 30, into image data expressing the density of the LORs for each of the pixels. In other words, on the basis of the LOR pattern in the reconstruction region 33 of the model 30, the generating function 106f calculates the density of the LORs for each of the pixels and generates the image data in which each of the pixels indicates the density of the LORs, as the sensitivity map 130a. In other words, the sensitivity map 130a is the data in which, with respect to each of the pixels, the density of the LORs is registered as sensitivity.

The sensitivity map 130a generated in this manner is stored in the memory 130 in advance and is used, during the PET image data reconstructing process performed by the reconstruction processing function 106b, for normalizing non-uniformity of sensitivity caused by the geometric arrangement of the channels (the sets each made up of the model of one scintillator and the model of one SiPM). For example, by using the sensitivity map 130a, the reconstruction processing function 106b is configured to reconstruct the PET image data according to Expression (1) presented below:

$$\lambda_j^{k+1} = \frac{\lambda_j^k}{S_j} \sum_i C_i \frac{y_i}{\sum_m C_{im} \lambda_m^k} \qquad (1)$$

For example, Expression (1) is a recurrence relation to calculate the pixel value $\lambda^{k+1}$ of a pixel j in the PET image data to be eventually obtained as a result of the reconstruction, by using the pixel value $\lambda^k$ of the pixel j and the reciprocal ($1/S_j$) of the pixel value $S_j$ of the pixel in the sensitivity map S. Expression (1) is an expression indicating an algorithm implementing a Maximum Likelihood—Expectation Maximization (ML-EM) scheme in a statistical successive approximation method. In Expression (1), the detection probability $C_{im}$ may be called a system matrix and denotes a probability that a photon occurring from an m-th pixel is counted by an i-th LOR. The element $y_i$ denotes an actual counted value, i.e., the number of events counted by the i-th LOR during the actual acquisition. According to the ML-EM scheme, a certain radiation distribution is postulated as an initial value. In other words, $\lambda$ (k=0) is assumed. According to the ML-EM scheme, with respect to the postulated distribution, the number of events expected to be counted by the i-th LOR is calculated by calculating the sum of $C_{im}$ and contribution of the pixel m. According to the ML-EM scheme, a ratio between the calculated number of events and the number of actual counted events (the number of actual counted events indicated by the numerator in Expression (1)) is calculated with respect to each of the LORs. If the ratio is 1 with respect to each of all the LORs, it means that the postulated pixel values reproduce the actual counted events. In that situation, the postulated pixel values reproduce the actual radiation distribution of the imaged subject. As for the operation of Expression (1), the pixel value $S_j$ of the sensitivity map S is defined as $\Sigma_i C_{ij}$ if there is no channel loss. As a result, the factor on the right starting with $\Sigma$ is equal to $S_j$, while a k-th pixel value is equal to a (k+1)-th pixel value, which means that the calculation is converged.

As explained above, the reconstruction processing function 106b is configured to reconstruct the PET image data, by using the reciprocal of the sensitivity of each of the pixels indicated in the sensitivity map 130a.

The exemplary configuration of the PET apparatus 100 according to the present embodiment has thus been explained. For example, the PET apparatus 100 is installed in a medical facility such as a hospital or a clinic and is used in various types of image diagnosis processes using the PET image data generated by the PET apparatus 100, for the patient P who is a patient hospitalized or visiting the medical facility. In the present embodiment, the PET apparatus 100 is configured to perform various types of processes described below, so as to be able to quantitatively and objectively evaluate impacts on image quality (or images) imposed by defective channels.

Figure 4:
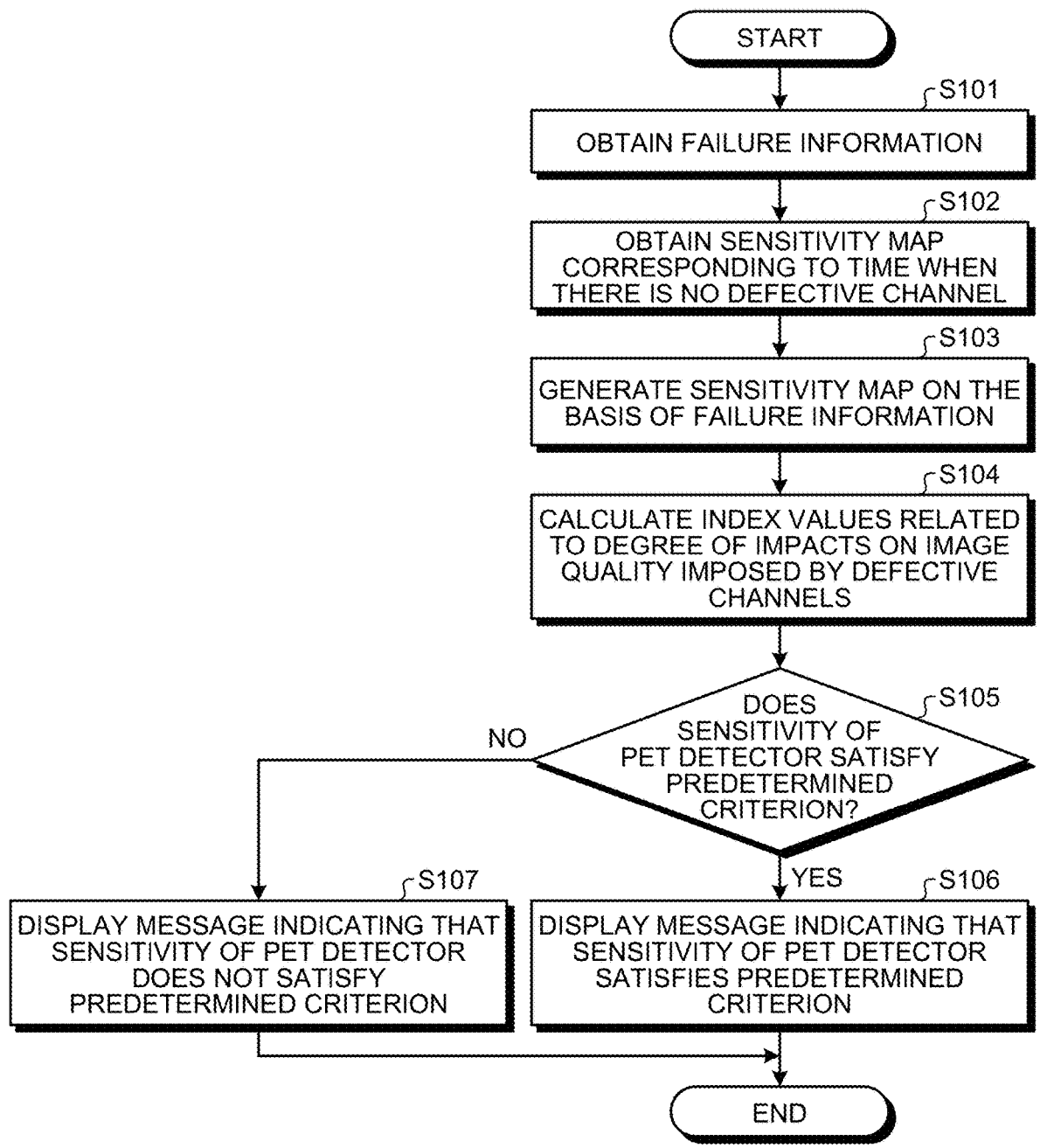
FIG. 4 is a flowchart illustrating an example of a flow in a process performed by the PET apparatus according to the first embodiment.

Next, an example of an evaluating process performed by the PET apparatus 100 will be explained. FIG. 4 is a flowchart illustrating an example of a flow in the evaluating process performed by the PET apparatus 100 according to the first embodiment. For example, the PET apparatus 100 is configured to perform the evaluating process, when the user inputs, to the processing circuitry 106, an instruction (an execution instruction) to perform the evaluating process presented in FIG. 4, via the input interface 110. In this situation, for example, the user inputs the execution instruction to the processing circuitry 106 via the input interface 110, so as to understand whether or not the impacts on image quality imposed by defective channels satisfy a predetermined quality criteria, after the PET apparatus 100 is installed in an imaging room of the medical facility, after regular maintenance of the PET apparatus 100, after the PET apparatus 100 is repaired, after an emergency countermeasure is taken when the PET apparatus 100 had a failure, or the like. In other examples, besides the abovementioned occasions, the user may input the execution instruction to the processing circuitry 106 via the input interface 110, so as to understand whether or not the impacts on image quality imposed by defective channels satisfy the predetermined quality criteria, when performing an acceptance test on the PET detector 101 by itself, when testing the PET detector 101 by itself before shipment, when inspecting the PET apparatus 100 before a work day starts, when determining a repair plan for the PET apparatus 100, or the like.

Step S101:

As illustrated in FIG. 4, at step S101, the obtaining function 106e obtains failure information (defect information) serving as information about defective channels. At the time of performing the evaluating process, there may be one or more defective channels among the channels of the PET detector 101 in some situations, and all the channels may be normal channels in other situations. In the following sections, an example will be explained in which there are one or more defective channels among the channels of the PET detector 101 at the time of performing the evaluating process. The failure information about the defective channels include, for example, the positions in which the defective channels are arranged and the quantity thereof. For example, the obtaining function 106e performs a health check to inspect whether or not the PET detector 101 is working properly and obtains the failure information about the defective channels. After that, the obtaining function 106e stores the obtained failure information into the memory 130. In this manner, at step S101, the obtaining function 106e obtains the failure information about the defective channels of the PET detector 101 at a point in time when the defective channels are present, which is later than the point in time which corresponds to the sensitivity map 130a stored in the memory 130 and at which all the channels of the PET detector 101 were normal channels. The point in time when the defective channels are present is an example of the second point in time.

Step S102:

Subsequently, at step S102, the obtaining function 106e obtains, from the memory 130, the sensitivity map 130a that is a sensitivity map of the PET detector 101 corresponding to the time when all the channels of the PET detector 101 were normal.

Step S103:

After that, at step S103, on the basis of the failure information, the generating function 106f generates a sensitivity map of the PET detector 101 corresponding to the point in time when the defective channels are present. In other words, at step S103, the sensitivity map reflecting the defective channels is generated, while the defective channels that are actually present are taken into consideration. For instance, the sensitivity map generated at step S103 is an example of the second sensitivity map. The following sections will explain a specific example of the process at step S103. To begin with, for example, the generating function 106f obtains the failure information from the memory 130.

After that, by using the same method as the method for generating the sensitivity map 130a explained with reference to FIG. 3, the generating function 106f generates the sensitivity map taking the defective channels indicated in the failure information into consideration. For example, the generating function 106f identifies the plurality of normal channels excluding the defective channels identified in the failure information, from among the 48 channels in the model 30 of the PET detector 101.

After that, the generating function 106f draws a LOR 32 connecting two channels among the identified plurality of normal channels, with respect to every combination each made up of two channels. Further, the generating function 106f generates the sensitivity map, by converting the LOR pattern in the reconstruction region 33 of the model 30, into image data expressing the density of the LORs for each of the pixels. In other words, on the basis of the LOR pattern in the reconstruction region 33 of the model 30, the generating function 106f calculates the density of the LORs for each of the pixels, as sensitivity of the PET detector 101, and generates the image data in which each of the pixels indicates the sensitivity, as the sensitivity map. According to the method described herein, the generating function 106f generates, at step S103, the sensitivity map registering the sensitivity with respect to each of the pixels, while taking the defective channels into consideration.

In this situation, the positional arrangements and the quantity of the plurality of pixels structuring the sensitivity map generated at step S103 are the same as the positional arrangements and the quantity of the plurality of pixels structuring the sensitivity map 130a. Accordingly, the plurality of pixels structuring the sensitivity map generated at step S103 correspond, respectively, to the plurality of pixels structuring the sensitivity map 130a.

In this situation, the sensitivity map 130a used at the time of reconstructing the PET image data is a sensitivity map that was generated in advance and saved in the memory 130 and that corresponds to the time when all the channels were normal channels. For this reason, differences in sensitivity indicated in the sensitivity map generated at step S103 in comparison to the sensitivity indicated in the sensitivity map 130a are exhibited in the sensitivity map generated at step S103, as the differences in sensitivity caused by the defective channels.

Figure 5:
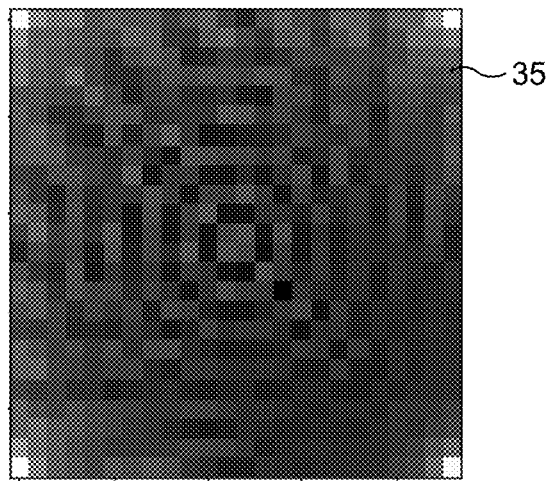
FIG. 5 is a drawing illustrating an example of a sensitivity map generated at step S103 according to the first embodiment.
Figure 6:
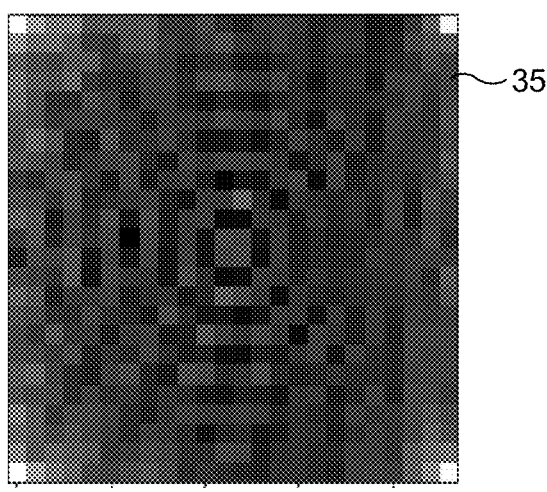
FIG. 6 is another drawing illustrating the example of the sensitivity map generated at step S103 according to the first embodiment.

The following sections will explain the situation where the sensitivity map generated at step S103 may vary when the positional arrangements of the defective channels are different, even when the quantity of the defective channels is the same. FIGS. 5 and 6 are drawings illustrating an example of the sensitivity map generated at step S103 according to the first embodiment.

A sensitivity map 35 illustrated in FIG. 5 is a sensitivity map generated at step S103 when the channel identified with an identifier "1" and the channel identified with an identifier "5" are defective channels. In contrast, another sensitivity map 35 illustrated in FIG. 6 is a sensitivity map generated at step S103 when the channel identified with the identifier "1" and the channel identified with an identifier "10" are defective channels. As understood when the sensitivity map 35 in FIG. 5 is compared with the sensitivity map 35 in FIG. 6, it is observed that the two sensitivity maps 35 are different from each other, when the positional arrangements of the defective channels are different even through the quantity of the defective channels is the same. The reason why the two sensitivity maps 35 are different from each other in this manner is, for example, that the relative positions of the defective channels are different between the sensitivity map 35 in FIG. 5 and the sensitivity map 35 in FIG. 6.

Step S104:

Subsequently, at step S104, the calculating function 106g calculates index values related to a degree of impacts on the image quality imposed by the defective channels, on the basis of the sensitivity map 130a and the sensitivity map generated at step S103. The following sections will explain a specific example of the process at step S104. For example, the calculating function 106g generates image data by dividing the sensitivity map generated at step S103 by the sensitivity map 130a. The positional arrangements and the quantity of the plurality of pixels structuring the image data generated by the calculating function 106g are the same as the positional arrangements and the quantity of the plurality of pixels structuring the sensitivity map 130a. Also, each of the pixel values of the plurality of pixels structuring the image data generated by the calculating function 106g is a value obtained by dividing the sensitivity indicated by a corresponding one of the plurality of pixels structuring the sensitivity map generated at step S103, by the sensitivity indicated by a corresponding one of the plurality of pixels structuring the sensitivity map 130a. In other words, the calculating function 106g calculates the index values each corresponding to a different one of the pixels, on the basis of ratios between the sensitivity map 130a and the sensitivity map generated at step S103.

At step S104, by generating the image data described above, the calculating function 106g calculates the pixel values of the plurality of pixels structing the image data as the index values related to the degree of impacts on the image quality imposed by the defective channels. In other words, the calculating function 106g evaluates, with respect to each of the pixels, the difference in sensitivity caused by the defective channels and calculates the evaluation result of each of the pixels as the index value.

In this situation, each of the index values falls in the range from 0 to 1 inclusive. As an index value approaches 1, the degree of impacts on the image quality imposed by the defective channels becomes smaller. Conversely, as an index value approaches 0, the degree of impacts on the image quality imposed by the defective channels becomes larger.

Alternatively, the calculating function 106g may calculate an index value for each of the pixels, on the basis of the differences between the sensitivity map 130a and the sensitivity map generated at step S103. In an example, the calculating function 106g may generate image data by subtracting the sensitivity map generated at step S103 from the sensitivity map 130a. In that situation, the pixel value of each of the plurality of pixels structuring the image data generated by the calculating function 106g is a value obtained by subtracting the sensitivity indicated by a corresponding one of the plurality of pixels structuring the sensitivity map generated at step S103, from the sensitivity indicated by a corresponding one of the plurality of pixels structuring the sensitivity map 130a. In this situation, each of the index values is a value equal to or larger than 0. As an index value approaches 0, the degree of impacts on the image quality imposed by the defective channels becomes smaller. Conversely, as an index value increases, the degree of impacts on the image quality imposed by the defective channels becomes larger.

Step S105:

Subsequently, at step S105, the judging function 106h judges whether or not the sensitivity of the PET detector 101 satisfies a predetermined criterion, on the basis of the index values. The following sections will explain a specific example of the process at step S105. For example, an example will be explained in which the PET apparatus 100 is required to have specifications where it is possible to quantitatively detect an aggregation of pixels with a pixel size of 4 mm×4 mm, while it is also required that a Standardized Uptake Value (SUV) evaluation can properly be performed.

In this situation, for example, a necessary condition of the PET detector 101 is set as that all the index values calculated in correspondence with the pixels at step S104 are each equal to or larger than a threshold value $\alpha$. The threshold value $\alpha$ may be "0.9", for example, but the threshold value $\alpha$ is not limited to this example. In this situation, at step S105, the judging function 106h judges whether or not the sensitivity of the PET detector 101 satisfies the predetermined criterion, by judging whether or not all the index values calculated in correspondence with the pixels are each larger than the threshold value α. For example, when determining that all the index values calculated in correspondence with the pixels are each larger than the threshold value α, the Judging function 106h determines that the sensitivity of the PET detector 101 satisfies the predetermined criterion. On the contrary, when determining that at least one among all the index values calculated in correspondence with the pixels is equal to or smaller than the threshold value α, the judging function 106h determines that the sensitivity of the PET detector 101 does not satisfy the predetermined criterion.

When having determined that the sensitivity of the PET detector 101 satisfies the predetermined criterion (step S105: Yes), the judging function 106h proceeds to step S106. On the contrary, when having determined that the sensitivity of the PET detector 101 does not satisfy the predetermined criterion (step S105: No), the judging function 106h proceeds to step S107.

Step S106:

At step S106, the display controlling function 106i causes the display device 120 to display a message indicating the judgment result obtained by the judging function 106h, i.e., a message indicating that the sensitivity of the PET detector 101 satisfies the predetermined criterion. For example, at step S106, the display controlling function 106i causes the display device 120 to display, as the message, a character string "The sensitivity of the PET detector 101 satisfies the criterion". Thus, the display controlling function 106i ends the process presented in FIG. 4.

Step S107:

At step S107, the display controlling function 106i causes the display device 120 to display a message indicating the judgment result obtained by the judging function 106h, i.e., a message indicating that the sensitivity of the PET detector 101 does not satisfy the predetermined criterion. For example, at step S107, the display controlling function 106i causes the display device 120 to display, as the message, a character string "The sensitivity of the PET detector 101 does not satisfy the criterion". Thus, the display controlling function 106i ends the process presented in FIG. 4.

As explained above, at step S106 and step S107, the display controlling function 106i causes the display device 120 to display the judgment result obtained by the judging function 106h.

The evaluating process presented in FIG. 4 is closed only with the geometric calculation using the result of the health check to inspect the defective channels of the PET detector 101. Further, the evaluating process is closed only with the calculation at the level of the PET detector 101 and is not dependent on whether an acquisition count is large or small, the magnitude of statistical noise varied by the acquisition count being large/small, or experience of the user who interprets the image. Accordingly, the PET apparatus 100 according to the first embodiment is able to quantitatively and objectively evaluate the impacts on the image quality and diagnosing capabilities imposed by the defective channels in the PET detector 101 having a large number of channels.

Further, the PET apparatus 100 is able to have the user acknowledge the message indicating that the sensitivity of the PET detector 101 satisfies the predetermined criterion or the message indicating that the sensitivity of the PET detector 101 does not satisfy the predetermined criterion. Furthermore, the PET apparatus 100 is able to make it possible for the user who acknowledged the message to correctly determine a countermeasure to be taken for the PET apparatus 100. As a result, the user is able to take the countermeasure to ensure that safety and capabilities of the PET apparatus 100 are guaranteed in the clinical field. Also, the user is able to properly allocate costs in the field of manufacture or services.

The PET apparatus 100 according to the first embodiment has thus been explained. As explained above, the PET apparatus 100 according to the first embodiment is able to quantitatively and objectively evaluate the impacts on the image quality (or the image) imposed by the defective channels.

Further, after the PET apparatus 100 has performed the evaluating process presented in FIG. 4, the reconstruction processing function 106b may reconstruct PET image data by using, instead of the sensitivity map 130a, the sensitivity map generated at step S103 that reflects the state of the channels of the PET detector 101 more accurately than the sensitivity map 130a does. For example, on the basis of the sensitivity map generated at step S103, the reconstruction processing function 106b may reconstruct the PET image data according to Expression (2) presented below.

$$\lambda_j^{k+1} = \frac{\lambda_j^k}{S'_j} \sum_i C_i \frac{y_i}{\sum_m C_{im} \lambda_m^k} \quad (2)$$

In Expression (2), the element $S'_j$ denotes the pixel value of the pixel in a sensitivity map $S'$ generated at step S103 reflecting the state of the channels of the PET detector 101 more accurately than the sensitivity map 130a does. In this manner, the reconstruction processing function 106b is configured to reconstruct the PET image data by using the reciprocal of the sensitivity of each of the pixels indicated in the sensitivity map generated at step S103. As a result, the reconstruction processing function 106b reconstructs the PET image data by using the sensitivity map reflecting the state of the channels of the PET detector 101 more accurately than the sensitivity map 130a does. It is therefore possible to reconstruct the PET image data with a higher level of precision.

Alternatively, when it is determined at step S105 that the sensitivity of the PET detector 101 does not satisfy the predetermined criterion (step S105: No), the reconstruction processing function 106b may reconstruct PET image data by using the sensitivity map generated at step S103. When the technique is applied to the state in which the PET apparatus 100 has defective channels, interpreting the PET image is made easier because uniformity of the image is restored by re-normalization that reflects the defective channels.

A Modification Example of the First Embodiment

After the PET apparatus 100 has performed the evaluating process (an evaluating process for the first time) presented in FIG. 4, there are some situations in which the user replaces the defective channels with normal channels or the user changes the positions of the defective channels. In those situations, by performing the evaluating process again (a second-time evaluating process), the PET apparatus 100 may generate, at step S103 in the second-time evaluating process, a sensitivity map having enhanced sensitivity compared to the sensitivity map generated at step S103 in the first-time evaluating process. Thus, this modification example will be explained as a modification example of the first embodiment. In the description of the modification example of the first embodiment, differences from the first embodiment will primarily be explained. Explanations of some of the elements that are the same as those in the first embodiment may be omitted.

In the modification example of the first embodiment, when the message is displayed at step S107 indicating that the sensitivity of the PET detector 101 does not satisfy the predetermined criterion, as a result of the PET apparatus 100 performing the evaluating process for the first time, the user acknowledges this message. Thus, the user understands that the sensitivity of the PET detector 101 does not satisfy the predetermined criterion.

In this situation, the user may take any of various countermeasures. For example, in a first example of the countermeasures, to make all the channels normal channels, the user may replace the sets that are each made up of a scintillator and a SiPM and correspond to the defective channels, with normal sets each made up of a scintillator and a SiPM having no failure. In other words, the user replaces the defective channels with the normal channels. In another example, as a second example of the countermeasures, while some channels remain as defective channels, the user may change the positions of the sets that are each made up of a scintillator and a SiPM and correspond to the defective channels to different positions, so that the sensitivity of the PET detector 101 satisfies the predetermined criterion, and also change the positions of the normal sets that are each made up of a scintillator and a SiPM having no failure and used to be arranged in the abovementioned different positions, to the pre-change positions of the defective channels. In other words, the user interchanges the positions between the defective channels and the normal channels.

After that, the PET apparatus 100 performs the evaluating process for the second time. For example, when the user inputs, to the processing circuitry 106, an execution instruction to perform the second-time evaluating process via the input interface 110, the PET apparatus 100 performs the evaluating process for the second time. Further, at step S106 in the second-time evaluating process, when a message is displayed indicating that the sensitivity of the PET detector 101 satisfies the predetermined criterion, the user acknowledges this message. Thus, the user understands that the sensitivity of the PET detector 101 satisfies the predetermined criterion. Subsequently, after the second-time evaluating process is performed, the reconstruction processing function 106b reconstructs PET image data according to Expression (2) presented above, by using the sensitivity map generated at step S103 in the second-time evaluating process. In this situation, in Expression (2), the element $S'_j$ denotes the pixel value of the pixel j in the sensitivity map S' generated at step S103 in the second-time evaluating process. In this situation, the sensitivity map generated at step S103 in the second-time evaluating process is a sensitivity map having the enhanced sensitivity compared to the sensitivity map generated at step S103 in the first-time evaluating process. Accordingly, in the modification example of the first embodiment, it is possible to reconstruct the PET image data having excellent image quality.

Further, the sensitivity map generated at step S103 in the second-time evaluating process is a sensitivity map of the PET detector 101 in which the defective channels have been changed with the normal channels that have no defects. Alternatively, the sensitivity map generated at step S103 in the second-time evaluating process is a sensitivity map of the PET detector 101 in which the positions of the defective channels have been changed to the positions different from the positions of the defective channels observed at the point in time when the first-time evaluating process was performed. For instance, the point in time when the first-time evaluating process was performed is an example of the first point in time.

As explained above, in the modification example of the first embodiment, at step S101 in the first-time evaluating process, the obtaining function 106e obtains the failure information about the defective channels of the PET detector 101 corresponding to the point in time when the first-time evaluating process is performed.

After that, at step S103 in the first-time evaluating process, the generating function 106f generates the sensitivity map of the PET detector 101 corresponding to the point in time when the defective channels are present, on the basis of the failure information obtained at step S101 in the first-time evaluating process. In this situation, for instance, the sensitivity map generated at step S103 in the first-time evaluating process is an example of the first sensitivity map.

Further, at step S103 in the second-time evaluating process, on the basis of the failure information obtained at step S101 in the second-time evaluating process, the generating function 106f generates the sensitivity map having the enhanced sensitivity compared to the sensitivity map generated at step S103 in the first-time evaluating process. In this situation, for instance, the sensitivity map generated at step S103 in the second-time evaluating process is an example of the second sensitivity map.

The PET apparatus 100 according to the modification example of the first embodiment has thus been explained. As explained above, the PET apparatus 100 according to the modification example of the first embodiment is able to reconstruct the PET image data having excellent image quality. Further, because the PET apparatus 100 according to the modification example of the first embodiment performs the processes similar to those performed by the PET apparatus 100 according to the first embodiment, it is possible to achieve advantageous effects similar to those achieved by the PET apparatus 100 according to the first embodiment.

Second Embodiment

In the first embodiment, the example was explained in which the PET apparatus 100 is configured to display the judgment result. However, the PET apparatus 100 may display, in addition to the judgment result, an image based on image data generated at the time of calculating the index values at step S104. Accordingly, this embodiment will be explained as a second embodiment. In the description of the second embodiment, differences from the first embodiment will primarily be explained. Explanations of some of the elements that are the same as those in the first embodiment may be omitted.

Figure 7:
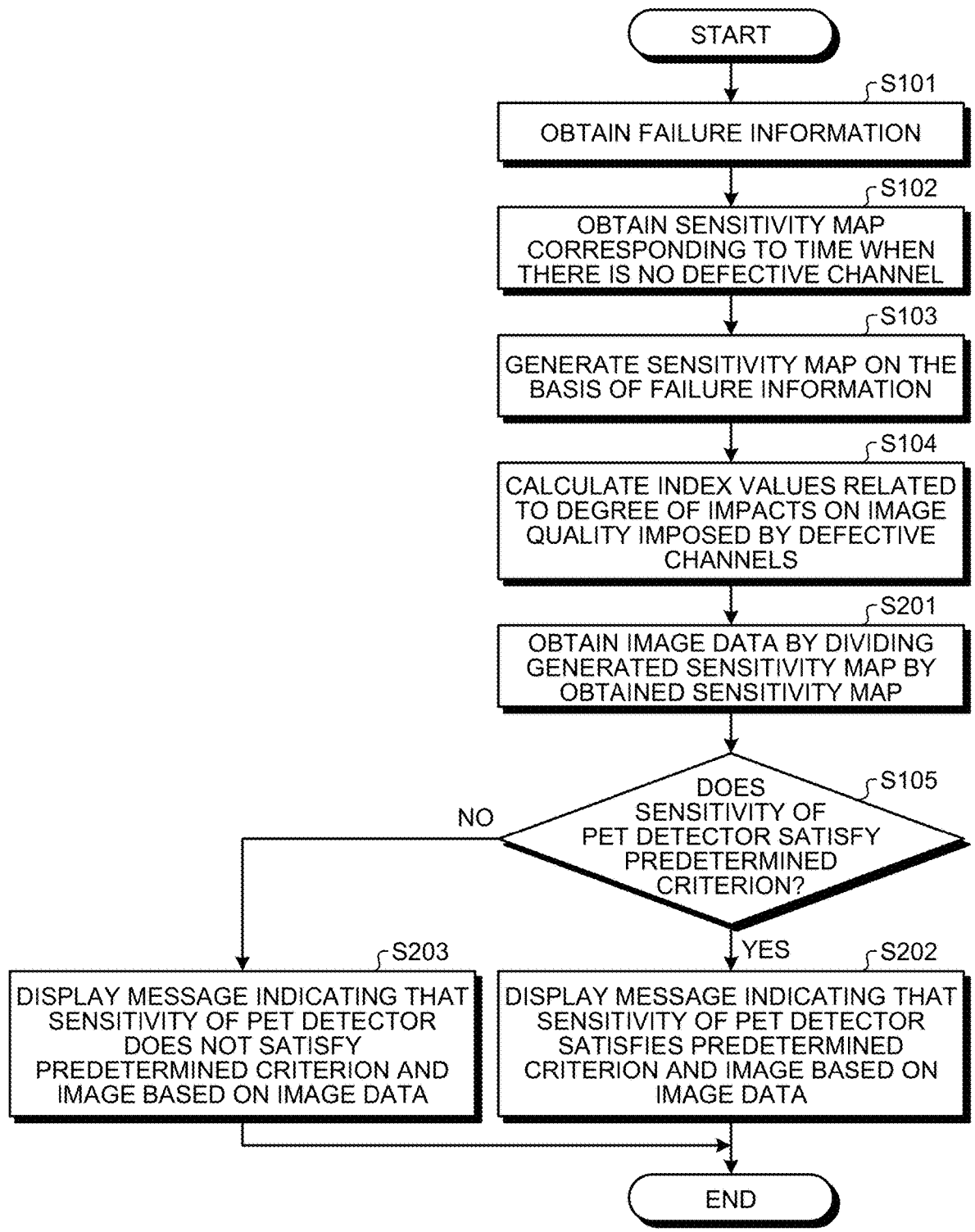
FIG. 7 is a flowchart illustrating an example of a flow in an evaluating process performed by a PET apparatus according to a second embodiment.

An example of an evaluating process performed by the PET apparatus 100 according to the second embodiment will be explained. FIG. 7 is a flowchart illustrating an example of a flow in the evaluating process performed by the PET apparatus 100 according to the second embodiment. In the second embodiment, for example, when the user inputs, to the processing circuitry 106, an execution instruction to perform the evaluating process via the input interface 110 with the same timing as that in the first embodiment, the PET apparatus 100 performs the evaluating process. The processes at steps S101 through S104 and step S105 in FIG. 7 according to the second embodiment are the same processes as those at steps S101 through S104 and step S105 in FIG. 4 according to the first embodiment. Thus, explanations of the processes at steps S101 through 3104 and step S105 according to the second embodiment will be omitted.

It should be noted, however, that the calculating function 106g stores, at step S104 in the second embodiment, the image data generated at the time of calculating the index values, into the memory 130. The image data is obtained either by dividing the sensitivity map generated at step S103 by the sensitivity map 130a or by subtracting the sensitivity map generated at step S103 from the sensitivity map 130a.

Step S201:

Further, as illustrated in FIG. 7, at step S201 performed between step S104 and step S105, the obtaining function 106e obtains the image data previously stored in the memory 130 at step S104.

When the judging function 106h determines that the sensitivity of the PET detector 101 satisfies the predetermined criterion (step S105: Yes), the display controlling function 106i proceeds to step S202. On the contrary, when the judging function 106h determines that the sensitivity of the PET detector 101 does not satisfy the predetermined criterion (step S105: No), the display controlling function 106i proceeds to step S203.

Step S202:

At step S202, the display controlling function 106i causes the display device 120 to display a message indicating that the sensitivity of the PET detector 101 satisfies the predetermined criterion and an image based on the image data obtained at step S201. After that, the display controlling function 106i ends the evaluating process presented in FIG. 7.

Step S203:

At step S203, the display controlling function 106i causes the display device 120 to display a message indicating that the sensitivity of the PET detector 101 does not satisfy the predetermined criterion and an image based on the image data obtained at step S201. After that, the display controlling function 106i ends the evaluating process presented in FIG. 7.

The PET apparatus 100 according to the second embodiment has thus been explained. The images displayed at step S202 and S203 each indicate a two-dimensional distribution of the index values. Accordingly, the PET apparatus 100 according to the second embodiment is able to make it possible for the user to visually understand the state of the PET detector 101 of the PET apparatus 100. Consequently, the PET apparatus 100 according to the second embodiment is able to make it possible for the user to understand the state of the PET detector 101 in detail. Further, the PET apparatus 100 according to the second embodiment is able to make it possible for the user to sufficiently understand the state of the PET detector 101. As a result, it is possible have the user use the PET apparatus 100 with the user's consent.

Further, during an inspection performed before the start of a work day or the like, macro capabilities of the PET detector 101 such as an energy resolution and a time resolution are usually checked. However, in addition to the macro capabilities, the PET apparatus 100 according to the second embodiment is able to make it possible for the user to understand micro capabilities such as the two-dimensional distribution of the index values.

Furthermore, because the PET apparatus 100 according to the second embodiment performs the processes similar to those performed by the PET apparatus 100 according to the first embodiment, it is possible to achieve advantageous effects similar to those achieved by the PET apparatus 100 according to the first embodiment.

Third Embodiment

In the first embodiment, the example was explained in which, when it is determined that the sensitivity of the PET detector 101 does not satisfy the predetermined criterion (step S105: No), the PET apparatus 100 is configured to display the message indicating that the sensitivity of the PET detector 101 does not satisfy the predetermined criterion. Further, in the second embodiment, the example was explained in which, when it is determined that the sensitivity of the PET detector 101 does not satisfy the predetermined criterion (step S105: No), the PET apparatus 100 is configured to display the message indicating that the sensitivity of the PET detector 101 does not satisfy the predetermined criterion and the image based on the image data obtained at step S201. Further, another arrangement is also acceptable in which, when it is determined that the sensitivity of the PET detector 101 does not satisfy the predetermined criterion (step S105: No), the PET apparatus 100 is configured to search for positional arrangements of the defective channels corresponding to a time when sensitivity of the PET apparatus 100 satisfies the predetermined criterion and to further cause the display device 120 to display information indicating the positional arrangements of the defective channels found in the search. Thus, this embodiment will be explained as a third embodiment.

As the PET apparatus 100 according to the third embodiment, the following will describe a PET apparatus 100 configured to perform processes at steps S301 and S302 described below, in place of the process at step S107 in the first embodiment. However, the PET apparatus 100 according to the third embodiment may alternatively be configured to perform the processes at steps S301 and S302 described below, in place of the process at step S203 in the second embodiment.

Further, in the description of the third embodiment, differences from the first embodiment will primarily be explained. Explanations of some of the constituent elements that are the same as those in the first embodiment may be omitted.

Figure 8:
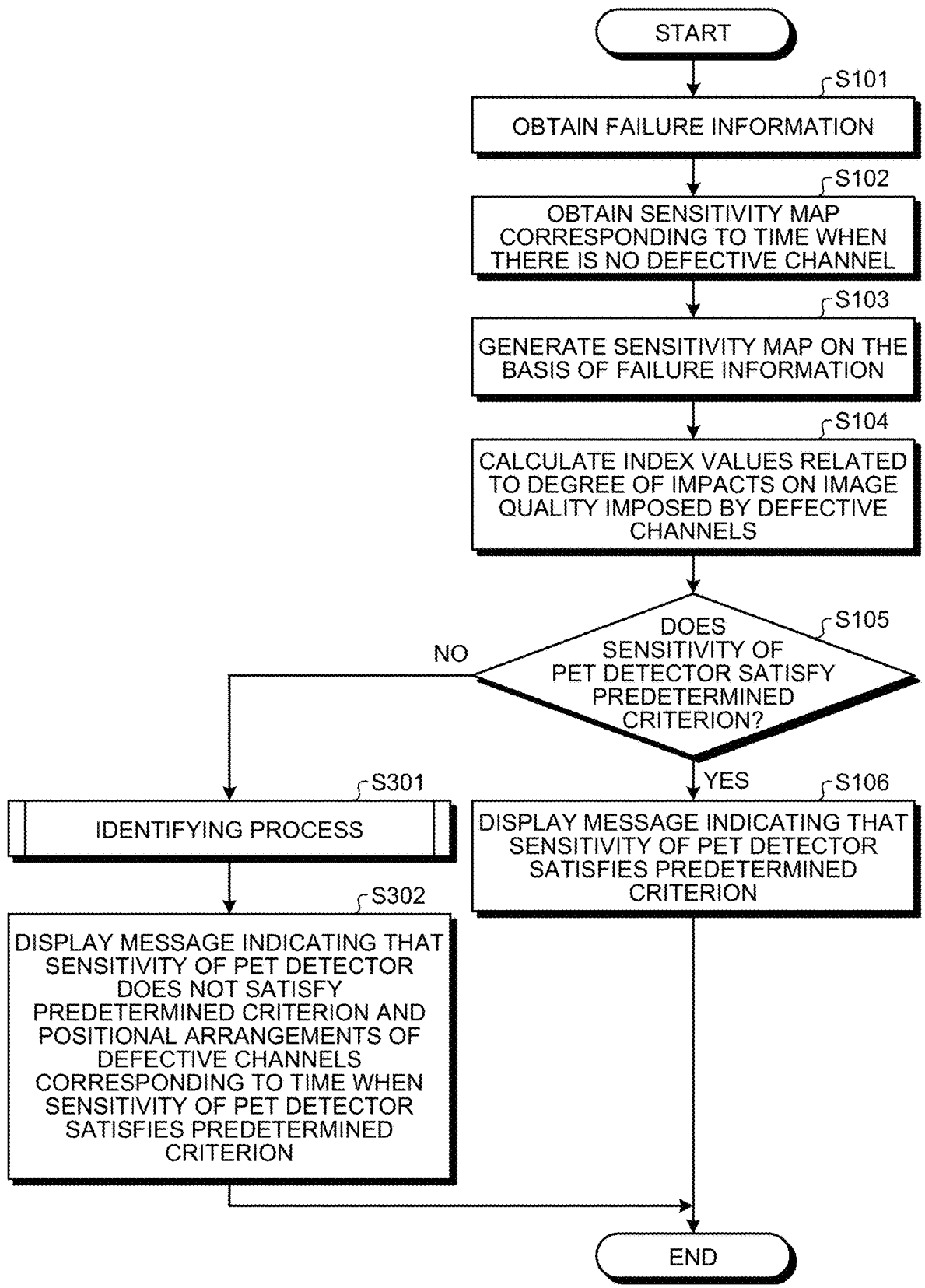
FIG. 8 is a flowchart illustrating an example of a flow in an evaluating process performed by a PET apparatus according to a third embodiment.

An example of the evaluating process performed by the PET apparatus 100 according to the third embodiment will be explained. FIG. 8 is a flowchart illustrating an example of a flow in the evaluating process performed by the PET apparatus 100 according to the third embodiment. In the third embodiment, for example, when the user inputs, to the processing circuitry 106, an execution instruction to perform the evaluating process via the input interface 110 with the same timing as that in the first embodiment, the PET apparatus 100 performs the evaluating process. The processes at steps S101 through S106 in FIG. 8 according to the third embodiment are the same processes as those at steps S101 through S106 in FIG. 4 according to the first embodiment. Thus, explanations of the processes at steps S101 through S106 according to the third embodiment will be omitted.

As illustrated in FIG. 8, in the third embodiment, when it is determined that the sensitivity of the PET detector 101 does not satisfy the predetermined criterion (step S105: No), the processing circuitry 106 proceeds to step S301.

Figure 9:
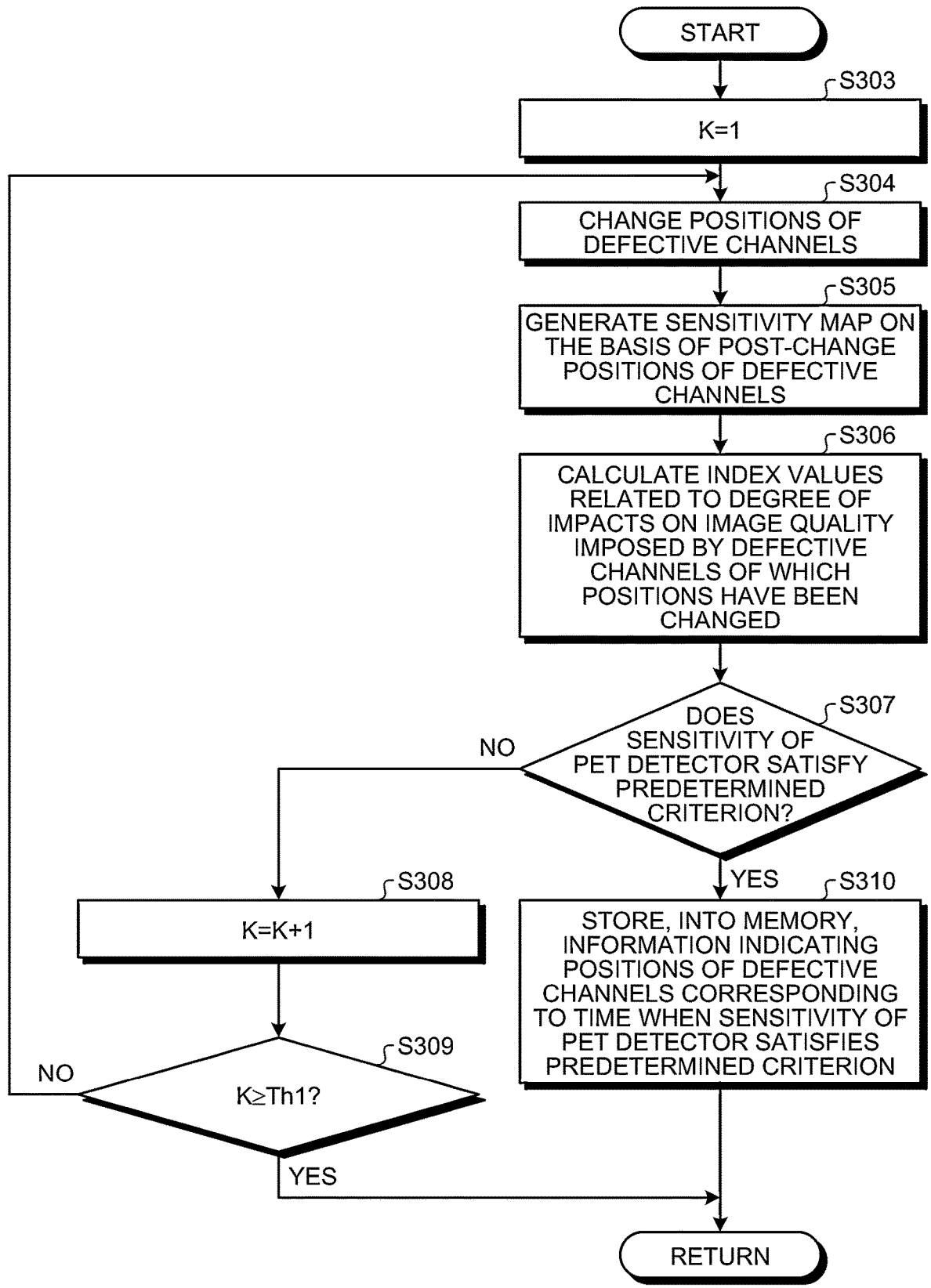
FIG. 9 is a flowchart illustrating an example of a flow in an identifying process performed at step S301 by the PET apparatus according to the third embodiment.

Step S301:

At step S301, the processing circuitry 106 performs an identifying process to identify the positions (the positional arrangements) of the defective channels corresponding to the time when the sensitivity of the PET detector 101 satisfies the predetermined criterion. FIG. 9 is a flowchart illustrating an example of a flow in the identifying process performed at step S301 by the PET apparatus 100 according to the third embodiment.

Step S303:

As illustrated in FIG. 9, at step S303, the generating function 106f sets a variable K to "1".

Step S304:

Subsequently, at step S304, the generating function 106f changes the positions (the positional arrangements) of the defective channels indicated in the failure information, within the model 30 of the PET detector 101. For example, the generating function 106f randomly changes the positions of the defective channels. More specifically, for example, the generating function 106f randomly generates random numbers from information about the present time or the like. In this situation, the generated plurality of random numbers are in one-to-one correspondence with a plurality of positions in which the channels can possibly be arranged. Accordingly, the generating function 106f identifies the positions corresponding to the generated random numbers. Further, the generating function 106f sets the defective channels in the identified positions. Thus, the positions of the defective channels have been changed. After that, among the plurality of positions in which the channels can possibly be arranged, the generating function 106f sets normal channels in the channels where no defective channels are set. In this manner, in the model of the PET detector 101, the generating function 106f has changed the positions of the defective channels without changing the quantity of the defective channels.

Step S305:

Subsequently, at step S305, the generating function 106f draws a LOR 32 connecting two channels among the plurality of normal channels other than the defective channels, with respect to every combination each made up of two channels. Further, the generating function 106f generates a sensitivity map, by converting the LOR pattern in the reconstruction region 33 of the model 30, into image data expressing the density of the LORs for each of the pixels. In other words, on the basis of the LOR pattern in the reconstruction region 33 of the model 30, the generating function 106f calculates the density of the LORs for each of the pixels, as sensitivity of the PET detector 101, and generates the image data in which each of the pixels indicates the sensitivity, as the sensitivity map.

In this manner, when it is determined that the sensitivity of the PET detector 101 does not satisfy the predetermined criterion (step S105: No), the generating function 106f changes the positions of the defective channels in the PET detector 101 at step S303 and generates the sensitivity map of the PET detector 101 on the basis of the post-change positions of the defective channels at step S305. For instance, the sensitivity map generated at step S305 is an example of the third sensitivity map.

Step S306:

After that, at step S306, the calculating function 106g calculates index values related to a degree of impacts on image quality imposed by the defective channels, on the basis of the sensitivity map 130a and the sensitivity map generated at step S305. For example, the calculating function 106g generates image data by dividing the sensitivity map generated at step S305 by the sensitivity map 130a, while using the same method as the method previously used at step S104 for generating the image data. In other words, the calculating function 106g calculates the index value for each of the pixels, on the basis of the ratios between the sensitivity map 130a and the sensitivity map generated at step S305.

Alternatively, the calculating function 106g may calculate an index value for each of the pixels, on the basis of differences between the sensitivity map 130a and the sensitivity map generated at step S305. For example, the calculating function 106g may generate image data by subtracting the sensitivity map generated at step S305 from the sensitivity map 130a, while using the same method as the method previously used at step S104 for generating the image data by subtracting the sensitivity map generated at step S103 from the sensitivity map 130a.

As explained above, at step S306, the calculating function 106g calculates the index values related to the degree of impacts on the image quality imposed by the defective channels of which the positions were changed, on the basis of the sensitivity map 130a and the sensitivity map generated at step S305.

Step S307:

Subsequently, at step S307, the judging function 106h judges whether or not the sensitivity of the PET detector 101 satisfies the predetermined criterion, on the basis of the index values. For example, the judging function 106h judges whether or not the sensitivity of the PET detector 101 satisfies the predetermined criterion on the basis of the index values, while using the same method as the method previously used at step S105 for judging whether or not the sensitivity of the PET detector 101 satisfies the predetermined criterion.

As explained above, the judging function 106h judges whether or not the sensitivity of the PET detector 101 satisfies the predetermined criterion, on the basis of the index values calculated on the basis of the sensitivity map 130a and the sensitivity map generated at step S305.

When it is determined that the sensitivity of the PET detector 101 does not satisfy the predetermined criterion (step S307: No), the generating function 106f proceeds to step S308. On the contrary, when it is determined that the sensitivity of the PET detector 101 satisfies the predetermined criterion (step S307: Yes), the generating function 106f proceeds to step S310.

Step S308:

At step S308, the generating function 106f increments the value of the variable K by 1.

Step S309:

Subsequently, at step S309, the generating function 106f judges whether or not the value of the variable K is equal to or larger than a threshold value Th1. The threshold value Th1 is a positive integer value used for determining an upper limit value for the number of times the processes at steps S303 through S308 are repeatedly performed. In the present embodiment, the processes at steps 3303 through S308 may repeatedly be performed up to ("the threshold value Th1"–1) times at most.

When the value of the variable K is equal to or larger than the threshold value Th1 (step S309: Yes), the generating function 106f makes a return. On the contrary, when the value of the variable K is smaller than the threshold value Th1 (step S309: No), the generating function 106f returns to step S304 described earlier and performs the processes at step S304 and thereafter.

Step S310:

At step S310, the generating function 106f stores, in the memory 130, information indicating the positions (the positional arrangements) of the defective channels corresponding to the time when the sensitivity of the PET detector 101 satisfies the predetermined criterion. For example, the generating function 106f generates information indicating the positions of the defective channels that were changed in the most recent process at step S304 and stores the generated information into the memory 130. After that, the generating function 106f makes a return.

In this situation, when the judgment at step S309 is in the affirmative and the process makes a return, the memory 130 does not store therein the information indicating the positions of the defective channels corresponding to the time when the sensitivity of the PET detector 101 satisfies the predetermined criterion. On the contrary, when the judgment at step S307 is in the affirmative and the process makes a return, the memory 130 stores therein the information indicating the positions of the defective channels corresponding to the time when the sensitivity of the PET detector 101 satisfies the predetermined criterion.

Step S302:

Returning to the description of FIG. 8, when the memory 130 has stored therein the information indicating the positions of the defective channels corresponding to the time when the sensitivity of the PET detector 101 satisfies the predetermined criterion, the display controlling function 106i causes the display device 120 to display, at step S302 as illustrated in FIG. 8, a message indicating that the sensitivity of the PET detector 101 does not satisfy the predetermined criterion and the information indicating the positions of the defective channels corresponding to the time when the sensitivity of the PET detector 101 satisfies the predetermined criterion. After that, the display controlling function 106i ends the evaluating process presented in FIG. 8.

As explained above, the display controlling function 106i causes the display device 120 to display the information indicating the post-change positions of the defective channels in the PET detector 101 corresponding to the time when the judging function 106h determines that the sensitivity of the PET detector 101 satisfies the predetermined criterion.

On the contrary, when the information indicating the positional arrangements of the defective channels corresponding to the time when the sensitivity of the PET detector 101 satisfies the predetermined criterion is not stored in the memory 130, the display controlling function 106i causes the display device 120 to display, at step S302, a message indicating that the sensitivity of the PET detector 101 does not satisfy the predetermined criterion. After that, the display controlling function 106i ends the evaluating process presented in FIG. 8.

The PET apparatus 100 according to the third embodiment has thus been explained. As a countermeasure against the defective channels, the PET apparatus 100 according to the third embodiment makes it possible for the user to understand the positional arrangements of the defective channels that alleviate the impacts on the image quality. As a result, it is possible to suppress clinical downtime that may be caused by repair work performed by the user.

Further, because the PET apparatus 100 according to the third embodiment performs the processes similar to those performed by the PET apparatus 100 according to the first embodiment or the second embodiment, it is possible to achieve advantageous effects similar to those achieved by the PET apparatus 100 according to the first embodiment or the second embodiment.

Alternatively, after the PET apparatus 100 has performed the evaluating process presented in FIG. 8, the reconstruction processing function 106b may reconstruct PET image data by using, instead of the sensitivity map 130a, the sensitivity map generated at step S305 corresponding to the time when the judging function 106h determines that the sensitivity of the PET detector 101 satisfies the predetermined criterion. For example, on the basis of the sensitivity map generated at step S305 corresponding to the time when the sensitivity of the PET detector 101 is determined to satisfy the predetermined criterion, the reconstruction processing function 106b may reconstruct the PET image data according to Expression (2) presented above. In that situation, in Expression (2), the element $S'_j$ denotes the pixel value of the pixel j in the sensitivity map S' generated at step S305 corresponding to the time when the sensitivity of the PET detector 101 is determined to satisfy the predetermined criterion.

Fourth Embodiment

Alternatively, in the embodiments and the modification examples described above, the PET apparatus 100 may be configured to further determine the quantity of defective channels tolerated in the PET detector 101. The tolerable quantity of defective channels may be used, for example, during an acceptance test performed at the time of accepting the PET detector 101, or the like. Thus, this embodiment will be explained as a fourth embodiment.

Figure 10:
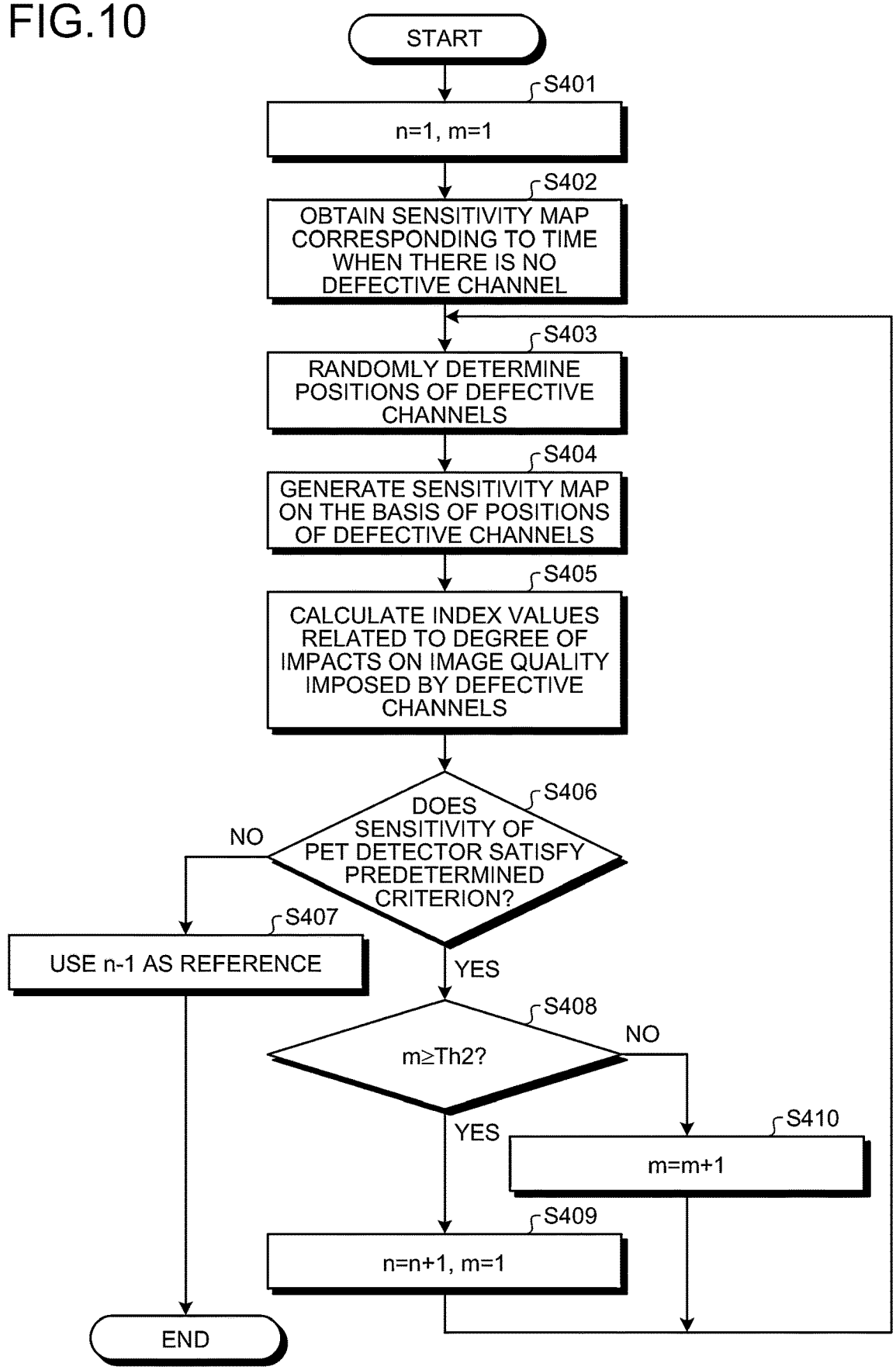
FIG. 10 is a flowchart illustrating an example of a flow in a tolerable defective channel quantity determining process performed by a PET apparatus according to a fourth embodiment.

The PET apparatus 100 according to the fourth embodiment is configured to perform the various processes described in any of the embodiments and the modification examples presented above. Further, the PET apparatus 100 according to the fourth embodiment is configured to further perform a tolerable defective channel quantity determining process. An example of the tolerable defective channel quantity determining process performed by the PET apparatus 100 according to the fourth embodiment will be explained. FIG. 10 is a flowchart illustrating an example of a flow in the tolerable defective channel quantity determining process performed by the PET apparatus 100 according to the fourth embodiment. In the fourth embodiment, for example, when the user inputs, to the processing circuitry 106, an instruction to perform the tolerable defective channel quantity determining process via the input interface 110, the PET apparatus 100 performs the tolerable defective channel quantity determining process.

Step S401:

As illustrated in FIG. 10, at step S401, the obtaining function 106e sets a variable n and a variable m each to "1". The variable n denotes the quantity of defective channels in a model of one detector module. For example, the model 30 of the PET detector 101 includes models of the 48 detector modules. Accordingly, the model 30 of the PET detector 101 includes defective channels of which the quantity is equal to (48×n).

Step S402:

Subsequently, at step S402, the obtaining function 106e obtains, from the memory 130, the sensitivity map 130a of the PET detector 101 corresponding to the time when all the channels of the PET detector 101 are normal channels.

Step S403:

After that, at step S403, the generating function 106f randomly determines the position (a positional arrangement) of each of the "48×n" defective channels in the model 30 of the PET detector 101. More specifically, for example, the generating function 106f randomly generates random numbers from information about the present time and identifiers identifying the detector modules or the like. In this situation, the generated plurality of random numbers are in one-to-one correspondence with the plurality of positions in which the channels can possibly be arranged. Further, the generating function 106f identifies the position of each of the (48×n) defective channels corresponding to a pertinent one of the generated random numbers. After that, the generating function 106f sets a defective channel in a corresponding one of the identified (48×n) positions for the defective channels. As a result, the positions of the defective channels have been determined. Further, among the plurality of positions in which the channels can possibly be arranged, the generating function 106f sets normal channels in certain positions that are not set with the defective channels. In this manner, the generating function 106f determines, in the model of the PET detector 101, the positions of the defective channels without changing the quantity of the defective channels.

Step S404:

Subsequently, at step S404, the generating function 106f generates a sensitivity map on the basis of the position of the defective channels. The following will describe an example of the process performed at step S404. To begin with, the generating function 106f draws a LOR 32 connecting two channels among the plurality of normal channels other than the defective channels, with respect to every combination each made up of two channels. Further, the generating function 106f generates the sensitivity map, by converting the LOR pattern in the reconstruction region 33 of the model 30, into image data expressing the density of the LORs for each of the pixels. In other words, on the basis of the LOR pattern in the reconstruction region 33 of the model 30, the generating function 106f calculates the density of the LORs for each of the pixels, as sensitivity of the PET detector 101, and generates the image data in which each of the pixels indicates the sensitivity, as the sensitivity map.

Step S405:

Subsequently, at step S405, the calculating function 106g calculates index values related to a degree of impacts on the image quality imposed by the defective channels, on the basis of the sensitivity map 130a and the sensitivity map generated at step S404. For example, the calculating function 106g generates the image data by dividing the sensitivity map generated at step S404 by the sensitivity map 130a, while using the same method as the method previously used at step S104 for generating the image data. In other words, the calculating function 106g calculates the index value for each of the pixels, on the basis of the ratios between the sensitivity map 130a and the sensitivity map generated at step S404.

Alternatively, the calculating function 106g may calculate an index value for each of the pixels, on the basis of differences between the sensitivity map 130a and the sensitivity map generated at step S404. In an example, the calculating function 106g may generate image data by subtracting the sensitivity map generated at step S404 from the sensitivity map 130a, while using the same method as the method previously used at step S104 for generating the image data by subtracting the sensitivity map generated at step S103 from the sensitivity map 130a.

Step S406:

Subsequently, at step S406, the judging function 106h judges whether or not the sensitivity of the PET detector 101 satisfies the predetermined criterion, on the basis of the index values. For example, the judging function 106h Judges whether or not the sensitivity of the PET detector 101 satisfies the predetermined criterion on the basis of the index values, while using the same method as the method previously used at step S105 for judging whether or not the sensitivity of the PET detector 101 satisfies the predetermined criterion.

When it is determined that the sensitivity of the PET detector 101 satisfies the predetermined criterion (step S406: Yes), the generating function 106f proceeds to step S408.

Step S408:

At step S408, the generating function 106f judges whether or not the value of the variable m is equal to or larger than a threshold value Th2. When the value of the variable m is equal to or larger than the threshold value Th2 (step S408: Yes), the generating function 106f proceeds to step S409. On the contrary, when the value of the variable m is smaller than the threshold value Th2 (step S408: No), the generating function 106f proceeds to step S410.

Step S409:

At step S409, the generating function 106f increments the value of the variable n by 1 and sets the value of the variable m to "1". After that, the generating function 106f returns to step S403 and performs the processes at step S403 and thereafter.

Step S410:

At step S410, the generating function 106f increments the value of the variable m by 1. After that, the generating function 106f returns to step S403 and performs the processes at step S403 and thereafter.

Accordingly, while the value of the variable n is constant, the processes at steps 3403 through 3406 and steps S408 through S410 are repeatedly performed up to (Th2−1) times at most.

In this manner, at steps S403 through S406 and steps S408 through S410, the processing circuitry 106 according to the fourth embodiment generates a plurality of sensitivity maps corresponding to a plurality of defective channel arrangement patterns having mutually-different defective channel positions, by performing, multiple times, a process of changing the positions of the defective channels either in the PET detector 101 or in the plurality of detector modules included in the PET detector 101 and generating the sensitivity map of the PET detector 101 on the basis of the post-change positions of the defective channels, and further repeatedly performs the abovementioned sensitivity map generating process while increasing the quantity of the defective channels until the sensitivity of the PET detector 101 no longer satisfies the predetermined criterion in at least one of the plurality of defective channel arrangement patterns.

On the contrary, when it is determined that the sensitivity of the PET detector 101 does not satisfy the predetermined criterion (step S406: No), the generating function 106f proceeds to step S407.

Step S407:

At step S407, the judging function 106h determines the tolerable quantity of defective channels in each of the detector modules as (n−1) and determines the tolerable quantity of defective channels in the entirety of the PET detector 101 as (48×(n−1)). After that, the judging function 106h ends the tolerable defective channel quantity determining process presented in FIG. 10.

As explained above, at step S407, the processing circuitry 106 according to the fourth embodiment determines the quantity of defective channels tolerated either in the PET detector 101 or in each of the plurality of detector modules, on the basis of the quantity of the defective channels corresponding to the time when the sensitivity of the PET detector 101 no longer satisfies the predetermined criterion in at least one of the arrangement patterns.

The tolerable quantity of defective channels (48×(n−1)) determined in the tolerable defective channel quantity determined process is used, when the PET detector 101 is ordered from an external source so that an acceptance test is performed at the time of accepting the PET detector 101 from the external source or the like. For example, when the quantity of defective channels in each of the detector modules of which the external source notified the user is n' while n' is equal to or smaller than (n−1), the user will accept the PET detector 101 manufactured by the external source. On the contrary, when n' is larger than (n−1), the user will not accept the PET detector 101 manufactured by the external source. After that, the user will re-order a PET detector 101 in which the quantity of defective channels in each of the detector modules is (n−1) or smaller.

In another example, when the quantity of defective channels in the PET detector 101 of which the external source notified the user is N while N is equal to or smaller than (48×(n−1)), the user will accept the PET detector 101 manufactured by the external source. On the contrary, when N is larger than (48×(n−1)), the user will not accept the PET detector 101 manufactured by the external source. After that, the user will re-order a PET detector 101 in which the quantity of defective channel is (48×(n−1)) or smaller.

The PET apparatus 100 according to the fourth embodiment has thus been explained. The PET apparatus 100 according to the fourth embodiment is able to determine the tolerable quantity of defective channels either in the PET detector 101 by itself or each of the detector modules by itself.

Further, the PET apparatus 100 according to the fourth embodiment performs the processes similar to the processes performed by the PET apparatus 100 according to any of the first embodiment, the second embodiment, the third embodiment, and the modification example of the first embodiment. Consequently, the PET apparatus 100 according to the fourth embodiment achieves advantageous effects similar to those achieved by the PET apparatus 100 according to any of the first embodiment, the second embodiment, the third embodiment, and the modification example of the first embodiment.

At steps S106, S107, S202, S203, and S302, the display controlling function 106*i* may be configured to further cause the display device 120 to display the sensitivity map generated at step S103. The sensitivity indicated in the sensitivity map generated at step S103 is closer to the actual state of the PET detector 101 than the sensitivity indicated in the sensitivity map 130*a* is. For this reason, by causing the display device 120 to display the sensitivity map generated at step S103, it is possible to enable the user to understand the sensitivity closer to the actual state of the PET detector 101. Further, because the sensitivity map 130*a* is stored in the memory 130 in advance, the user is able to understand the distribution of sensitivity indicated in the sensitivity map 130*a* with desired timing. Consequently, the user is able to understand the sections having different sensitivity levels by comparing the sensitivity map 130*a* with the sensitivity map generated at step S103. Thus, the user is able to understand a range in which the impacts of the defective channels are exerted. Consequently, causing the display device 120 to display the sensitivity map generated at step S103 makes it possible to quantitatively and objectively evaluate the impacts on the image quality imposed by the defective channels.

Further, at step S106, S107, S202, S203, or S302, the display controlling function 106*i* may be configured to further cause the display device 120 to display the sensitivity map 130*a* obtained at step S102 and the sensitivity map generated at step S103 so as to be arranged side by side to make comparison possible. Causing the sensitivity map 130*a* and the sensitivity map generated at step S103 to be displayed in a comparable manner makes it possible for the user to understand the sections having mutually-different sensitivity levels. Consequently, it is possible to enable the user to understand a range in which the impacts of the defective channels are exerted.

Further, in the embodiments and the modification examples described above, the example was explained in which the PET apparatus 100 performs the various types of processes by using the two-dimensional sensitivity map. However, the PET apparatus 100 may perform the same processes by using a three-dimensional sensitivity map.

The program executed by the one or more processors are provided as being incorporated, in advance, in a Read Only Memory (ROM), a storage circuit, or the like. Further, the program may be provided as being recorded in a non-transitory computer-readable storage medium such as a Compact Disk Read-Only Memory (CD-ROM), a Flexible Disk (FD), a Compact Disk Recordable (CD-R), or a Digital Versatile Disk (DVD), in a file in a format that is installable or executable by those devices. Further, the program may be stored in a computer connected to a network such as the Internet so as to be provided or distributed as being downloaded via the network. For example, the program is structured with modules including the processing functions described above. In actual hardware, as a result of a CPU reading and executing the program from a storage medium such as a ROM, the modules are loaded into a main storage device and generated in the main storage device.

According to at least one aspect of the embodiments described above, it is possible to quantitatively and objectively evaluate the impacts on the image quality imposed by the defective channels.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A Positron Emission Tomography (PET) apparatus comprising processing circuitry configured:
   to obtain information about a defective channel of a PET detector at a second point in time later than a first point in time corresponding to a first sensitivity map that is a sensitivity map of the PET detector corresponding to the first point in time and being stored in a memory; and
   to generate a second sensitivity map that is a sensitivity map of the PET detector corresponding to the second point in time, on a basis of the information about the defective channel.

2. The PET apparatus according to claim 1, wherein the processing circuitry further causes a display device to display the second sensitivity map.

3. The PET apparatus according to claim 1, wherein the processing circuitry further calculates an index value related to a degree of an impact on image quality imposed by the defective channel, on a basis of the first sensitivity map and the second sensitivity map.

4. The PET apparatus according to claim 3, wherein the processing circuitry calculates the index value on a basis of either a ratio or a difference calculated between the first sensitivity map and the second sensitivity map.

5. The PET apparatus according to claim 3, wherein
   the processing circuitry further judges whether or not sensitivity of the PET detector satisfies a predetermined criterion, on a basis of the index value, and the processing circuitry causes a display device to display a result of the judgment.

6. The PET apparatus according to claim 5, wherein
when it is determined that the sensitivity of the PET detector does not satisfy the predetermined criterion, the processing circuitry changes a position of the defective channel in the PET detector and generates a third sensitivity map that is a sensitivity map of the PET detector, on a basis of a post-change position of the defective channel,
the processing circuitry calculates an index value related to a degree of an impact on image quality imposed by the defective channel of which the position has been changed, on a basis of the first sensitivity map and the third sensitivity map,
the processing circuitry judges whether or not the sensitivity of the PET detector satisfies the predetermined criterion, on a basis of the index value calculated on the basis of the first sensitivity map and the third sensitivity map, and
the processing circuitry causes the display device to display information indicating the post-change position of the defective channel in the PET detector corresponding to a time when the sensitivity of the PET detector is determined to satisfy the predetermined criterion.

7. The PET apparatus according to claim 1, wherein the processing circuitry further causes a display device to display one of: an image based on image data obtained by dividing the second sensitivity map by the first sensitivity map; and an image based on image data obtained by subtracting the first sensitivity map from the first sensitivity map.

8. The PET apparatus according to claim 1, wherein the processing circuitry further reconstructs PET image data on a basis of the second sensitivity map.

9. The PET apparatus according to claim 6, wherein the processing circuitry further reconstructs PET image data, on a basis of the third sensitivity map corresponding to the time when the sensitivity of the PET detector is determined to satisfy the predetermined criterion.

10. The PET apparatus according to claim 8, wherein the processing circuitry reconstructs the PET image data on a basis of a reciprocal of the second sensitivity map.

11. A method for acknowledging, displaying and reducing impacts imposed by a defective channel of a PET detector comprising:
obtaining information about the defective channel of the PET detector at a second point in time later than a first point in time corresponding to a first sensitivity map that is a sensitivity map of the PET detector corresponding to the first point in time and being stored in a memory; and
generating a second sensitivity map that is a sensitivity map of the PET detector corresponding to the second point in time, on a basis of the information about the defective channel.

12. A non-transitory recording medium having recorded thereon a program that causes a computer to perform:
obtaining information about a defective channel of a PET detector at a second point in time later than a first point in time corresponding to a first sensitivity map that is a sensitivity map of the PET detector corresponding to the first point in time and being stored in a storage unit; and
generating a second sensitivity map that is a sensitivity map of the PET detector corresponding to the second point in time, on a basis of the information about the defective channel.

* * * * *